(12) United States Patent
Van Ness et al.

(10) Patent No.: US 7,112,423 B2
(45) Date of Patent: Sep. 26, 2006

(54) NUCLEIC ACID AMPLIFICATION USING NICKING AGENTS

(75) Inventors: Jeffrey Van Ness, Claremont, CA (US); David J Galas, Claremont, CA (US); Lori K Van Ness, Claremont, CA (US)

(73) Assignee: Keck Graduate Institute, Claremont, CA (US)

( * ) Notice: Subject to any disclaimer, the term of this patent is extended or adjusted under 35 U.S.C. 154(b) by 176 days.

(21) Appl. No.: 10/197,239

(22) Filed: Jul. 15, 2002

(65) Prior Publication Data

US 2003/0104431 A1    Jun. 5, 2003

Related U.S. Application Data

(60) Provisional application No. 60/345,445, filed on Jan. 2, 2002, provisional application No. 60/335,685, filed on Nov. 13, 2001, provisional application No. 60/305,637, filed on Jul. 15, 2001.

(51) Int. Cl.
*C12P 19/34* (2006.01)
*C12Q 1/68* (2006.01)
*C07H 21/02* (2006.01)
*C07H 21/04* (2006.01)

(52) U.S. Cl. .................... 435/91.2; 435/6; 536/23.1

(58) Field of Classification Search ............. 435/91.2, 435/6, 91.1; 536/23.1, 24.3
See application file for complete search history.

(56) References Cited

U.S. PATENT DOCUMENTS

| | | | | |
|---|---|---|---|---|
| 4,935,357 A | 6/1990 | Szybalski | ................... | 435/91 |
| 5,011,769 A | 4/1991 | Duck et al. | ................... | 435/6 |
| 5,455,166 A | 10/1995 | Walker | ................... | 435/91.2 |
| 5,470,723 A | 11/1995 | Walker et al. | ............. | 435/91.2 |
| 5,523,204 A | 6/1996 | Singer et al. | ................... | 435/5 |
| 5,547,861 A | 8/1996 | Nadeau et al. | ............. | 435/91.2 |
| 5,561,044 A | 10/1996 | Walker et al. | ................... | 435/6 |
| 5,624,825 A | 4/1997 | Walker et al. | ............. | 435/91.2 |
| 5,631,147 A | 5/1997 | Lohman et al. | ............. | 435/91.2 |
| 5,648,211 A | 7/1997 | Fraiser et al. | ................... | 435/6 |
| 5,702,926 A | 12/1997 | Fraiser et al. | ............. | 435/91.2 |
| 5,712,214 A | 1/1998 | Huang et al. | ................... | 502/37 |
| 5,733,752 A | 3/1998 | Lohman et al. | ............. | 435/91.2 |
| 5,736,365 A | 4/1998 | Walker et al. | ............. | 435/91.2 |
| 5,744,311 A | 4/1998 | Fraiser et al. | ................... | 435/6 |
| 5,756,702 A | 5/1998 | Lohman et al. | ........... | 536/24.33 |
| 5,811,269 A | 9/1998 | Nadeau et al. | ............. | 435/91.1 |

(Continued)

FOREIGN PATENT DOCUMENTS

EP    0500224    8/1992

(Continued)

OTHER PUBLICATIONS

Iakobashvili, R. et al., "Low temperature cycle PCR protocol for Klenow fragment of DNA polymerase I in the presence of proline", Nucl. Acids Res., vol. 27, pp. 1566-1568 (1999).*

(Continued)

*Primary Examiner*—Teresa Strzelecka
(74) *Attorney, Agent, or Firm*—SEED Intellectual Property Law Group, PLLC

(57) ABSTRACT

The present invention provides methods and kits for amplifying target nucleic acids (including whole genomes) using nicking agents. In certain aspects, the amplification does not require the use of any external oligonucleotide primers that are capable of annealing to a portion of the target nucleic acid. This invention is useful in many areas such as genetic disease diagnoses, forensic analyses and paleoarcheological studies.

16 Claims, 1 Drawing Sheet

U.S. PATENT DOCUMENTS

| | | | |
|---|---|---|---|
| 5,837,469 A | 11/1998 | Harris | 435/6 |
| 5,849,547 A | 12/1998 | Cleuziat et al. | 435/91.21 |
| 5,916,779 A | 6/1999 | Pearson et al. | 435/91.2 |
| 5,919,630 A | 7/1999 | Nadeau et al. | 435/6 |
| 5,928,869 A | 7/1999 | Nadeau et al. | 435/6 |
| 5,958,700 A | 9/1999 | Nadeau et al. | 435/6 |
| 5,962,273 A | 10/1999 | Durmowicz et al. | 435/91.1 |
| 5,968,786 A | 10/1999 | Dunn et al. | 435/91.53 |
| 5,976,805 A | 11/1999 | You | 435/6 |
| 5,985,569 A | 11/1999 | Foxall et al. | 435/6 |
| 6,004,754 A | 12/1999 | You | 435/6 |
| 6,054,279 A | 4/2000 | Nadeau et al. | 435/6 |
| 6,063,573 A | 5/2000 | Kayyem | 435/6 |
| 6,063,604 A | 5/2000 | Wick et al. | 435/91.2 |
| 6,087,133 A | 7/2000 | Dattagupta et al. | 435/91.1 |
| 6,124,120 A | 9/2000 | Lizardi | 435/91.2 |
| 6,132,970 A | 10/2000 | Stemmer | 435/6 |
| 6,191,267 B1 | 2/2001 | Kong et al. | 536/23.4 |
| 6,197,557 B1 | 3/2001 | Makarov et al. | 435/91.2 |
| 6,214,587 B1 | 4/2001 | Dattagupta et al. | 435/91.2 |
| 6,218,125 B1 | 4/2001 | Foxall et al. | 435/6 |
| 6,221,592 B1 | 4/2001 | Schwartz et al. | 435/6 |
| 6,235,502 B1 * | 5/2001 | Weissman et al. | 435/91.1 |
| 6,238,868 B1 | 5/2001 | Carrino et al. | 435/6 |
| 6,238,884 B1 | 5/2001 | Short et al. | 435/69.1 |
| 6,258,546 B1 | 7/2001 | McMillian et al. | 435/6 |
| 6,280,949 B1 | 8/2001 | Lizardi | 435/6 |
| 6,297,053 B1 | 10/2001 | Stemmer | 435/440 |
| 6,316,200 B1 | 11/2001 | Nadeau et al. | 435/6 |
| 6,537,757 B1 | 3/2003 | Langmore et al. | 435/6 |
| 2001/0039039 A1 | 11/2001 | Weissman et al. | 435/91.1 |
| 2002/0006643 A1 | 1/2002 | Kayyem et al. | 435/91.2 |
| 2002/0187508 A1 * | 12/2002 | Wong | 435/6 |

FOREIGN PATENT DOCUMENTS

| | | |
|---|---|---|
| EP | 0585660 | 3/1994 |
| EP | 0640691 | 3/1995 |
| EP | 0819768 | 1/1998 |
| EP | 0878553 | 11/1998 |
| WO | WO 95/25180 | 9/1985 |
| WO | WO 89/10415 | 11/1989 |
| WO | WO97/11196 | 3/1997 |
| WO | WO97/35026 | 9/1997 |
| WO | WO 99/18241 | 4/1999 |
| WO | WO99/49081 | 9/1999 |
| WO | WO 00/15849 | 3/2000 |
| WO | WO00/28084 | 5/2000 |
| WO | WO 00/31300 | 6/2000 |
| WO | WO00/60919 | 10/2000 |
| WO | WO00/61720 | 10/2000 |
| WO | WO00/61803 | 10/2000 |
| WO | WO00/62036 | 10/2000 |
| WO | WO00/63437 | 10/2000 |
| WO | WO 01/90419 | 11/2001 |

OTHER PUBLICATIONS

Brenowitz, S. et al., "Specificity and Enzymatic Mechanism of Editing Exonuclease of *Escherichia coli* DNA polymerase III", J. Biol. Chem., vol. 266, pp. 7888-7892 (1991).*

McCarthy, M.J. et al., "A modified quantitative polymerase chain reaction assay for measuring gene-specific repair of UV photoproducts in human cells", Mutation Res., vol. 363, pp. 57-66 (1996).*

Tornaletti,S. & Pfeifer, G. P., "UV damage and repair mechanisms in mammalian cells", BioEssays, vol. 18, pp. 221-228 (1996).*

Abramson et al., "Nucleic Acid Amplification Technologies," *Curr. Opin. Biotech.* 4:41-47, 1993.

Akduman et al., "Evaluation of a Strand Displacement Amplification Assay (BD ProbeTec-SDA) for Detection of *Neisseria gonorrhoeae* in Urine Specimens," *J. Clin. Microbiol.* 40(1):281-283, Jan. 2002.

Andras et al., "Strategies for Signal Amplification in Nucleic Acid Detection," *Mol. Biotech.* 19:24-44, 2001.

Badak et al., "Confirmation of the Presence of *Mycobacterium tuberculosis* and Other Mycobacteria in Mycobacterial Growth Indicator Tubes (MGIT) by Multiplex Strand Displacement Amplification," *J. Clin. Microbiol.* 35(5):1239-43, May 1997.

Bergmann et al., "Clinical Evaluation of the BDProbeTec Strand Displacement Amplification Assay for Rapid Diagnosis of Tuberculosis," *J. of Clin. Microbiol.* 36(9):2766-2768, Sep. 1998.

Besnier et al., "Converting *Mly*I Endonuclease Into a Nicking Enzyme by Changing Its Oligomerization State," *EMBO Reports* 2(9): 782-786, 2001.

Chan et al., "Performance Characteristics of the Becton Dickinson ProbeTec System for Direct Detection of *Chlamydia trachomatis* and *Neisseria gonorrhoea* in Male and Female Urine Specimens in Comparison With the Roche Cobas System," *Arch. Pathol. Lab. Med.* 124:1649-1652, Nov. 2000.

Down et al., "Detection of *Mycobacterium tuberculosis* in Respiratory Specimens by Strand Displacement Amplification of DNA," *J. Clin. Microbiol.* 34(4):860-865, Apr. 1996.

Edman et al., "Pathogen Analysis and Genetic Predisposition Testing Using Microelectronic Arrays and Isothermal Amplification," *J. Invest. Med.* 48(2):93-101, Mar. 2000.

Gelb et al., "Editorial Summary of the Pre-symposium Workshop on the Contemporary Assessment of Technologies," *Biologicals* 24:177-186, 1996.

Hellyer et al., "Detection of Viable *Mycobacterium tuberculosis* by Reverse Transcriptase-Strand Displacement Amplification of mRNA," *J. Clin. Microbiol.* 37(3):518-523, Mar. 1999.

Hellyer et al., "Specificity of IS6110-Based Amplification Assays for *Mycobacterium tuberculosis* Complex," *J. Clin. Microbiol.* 34(11): 2843-2846, Nov. 1996.

Hellyer et al., "Strand Displacement Amplification and the Polymerase Chain Reaction for Monitoring Response to Treatment in Patients with Pulmonary Tuberculosis," *J. Infec. Diseases* 173:934-941, Apr. 1996.

Higgins et al., "The Nicking Endonuclease N.*Bst*NBI is closely related to Type IIs Restriction Endonucleases *Mly*I and *Ple*I," *Nucl. Acids Res.* 29(12):2492-2501, 2001.

Huang et al., "Multiple Cleavage Activities of Endonuclease V from *Thermotoga maritima* Recognition an Strand Nicking Mechanism," *Biochemistry* 40:8738-8748, 2001.

Ichiyama et al., "Diagnostic Value of the Strand Displacement Amplification Method Compared to Those of Roche Amplicor PCR and Culture for Detecting Mycobacteria in Sputum Samples," *J. of Clin. Microbiol.* 35(12):3082-3085, Dec. 1997.

Kim et al., "Site-Specific Cleavage of DNA-RNA Hybrids by Zinc Finger/*Fok*I Cleavage Domain Fusions," *Gene* 203:43-49, 1997.

Laken et al., "Genotyping by Mass Spectrometric Analysis of Short DNA Fragments," *Nature Biotechnology* 16:1352-1356, Dec. 1998.

Lavin et al, "A Mammalian Nicking Endonuclease," *Biochem.* 15(11):2409-2414, 1976.

Lisby, Gorm, "Application of Nucleic Acid Amplification in Clinical Microbiology," *Mol. Biotechnol.* 12:75-99, 1999.

Little et al., "Strand Displacement Amplification and Homogeneous Real-Time Detection Incorporated in a Second-Generation DNA Probe System, BDProbeTecET," *Clin. Chem.* 45(6):777-784, 1999.

Little et al., "Nucleotide Sequence and Strand Displacement Amplification of the 70K Protein Gene From Mycobacteria," *Mol. and Cell. Probes* 8:375-384, 1994.

Lizardi et al., "Mutation Detection and Single-Molecule Counting Using Isothermal Rolling-Circle Amplification," *Nature Genetics* 19:225-232, Jul. 1998.

Mehrpouyan et al., A Rapid and Sensitive Method for Non-Isotopic Quantitation of HIV-1 RNA Using Thermophilic SDA and Flow Cytometry, *Mol. and Cell Probes* 11:337-347, 1997.

Milla et al., "Use of the Restriction Enzyme *Ava*I and Exo *Bst* Polymerase in Strand Displacement Amplification," *BioTechniques* 24(3):392-396, Mar. 1998.

Morgan et al., "Characterization of the Specific DNA Nicking Activity of Restriction Endonuclease N.BstNBI," Biol. Chem. 381:1123-1125, Nov. 2000.

Nadeau et al., "Real-Time, Sequence-Specific Detection of Nucleic Acids During Strand Displacement Amplification," Anal. Biochem. 276:177-87, 1999.

Notomi et al., "Loop-Mediated Isothermal Amplification of DNA," Nuc. Acids Res. 28(12):i-vii, 2000.

Nuovo, Gerard, "In Situ Strand Displacement Amplification: An Improved Technique for the Detection of Low Copy Nucleic Acids," Diag. Mol. Path. 9(4):195-202, 2000.

Nycz et al., "Quantitative Reverse Transcription Strand Displacement Amplification: Quantitation of Nucleic Acids Using and Isothermal Amplification Technique," Anal. Biochem. 259:226-234, 1998.

Pfyffer et al., "Performance Characteristics of the BDProbeTec System for Direct Detection of Mycobacterium tuberculosis Complex in Respiratory Specimens," J. Clin. Microbiol. 37(1):137-140, Jan. 1999.

Seckinger, Daniel, "Strand Displacement Amplification and Fluorescence Polarization," Clin. Chem. 42(10):1720, 1996.

Spargo et al., "Chemiluminescent Detection of Strand Displacement Amplified DNA from Species Comprising the Mycobacterium tuberculosis Complex," Mol. and Cell. Probes 7:395-404, 1993.

Spargo et al., "Detection of M. tuberculosis DNA Using Thermophilic Strand Displacement Amplification," Mol. and Cell. Probes 10:247-256, 1996.

Spears et al., "Simultaneous Strand Displacement Amplification and Fluorescence Polarization Detection of Chlamydia trachomatis DNA," Anal. Biochem. 247:130-37, 1997.

Stahl et al., "Introduction of Asymmetry in the Naturally Symmetric Restriction Endonuclease EcoRV to Investigate Intersubunit Communication in the Homodimeric Protein," PNAS USA 93:6175-6180, Jun. 1996.

Thomas et al., "Amplification of Padlock Probes for DNA Diagnostics by Cascade Rolling Circle Amplification or the Polymerase Chain Reaction," Arch. Pathol. Lab. Med. 123:1170-1176, Dec. 1999.

Van Dyck et al., "Detection of Chlamydia trachomatis and Neisseria gonorrhoeae by Enzyme Immunoassay, Culture, and Three Nucleic Acid Amplification Tests," J. Clin. Microbiol. 39(5):1751-1756, May 2001.

Walker et al., "DNA Detection by Strand Displacement Amplificatin and Fluorescence Polarization With Signal Enhancement Using a DNA Binding Protein," Nucl. Acids Res. 24(2):348-353, 1996.

Walker et al., "A DNA Probe Assay Using Strand Displacement Amplification (SDA) and Filtration to Separate Reacted and Unreacted Detector Probes," Mol. and Cell. Probes 9:399-403, 1995.

Walker et al., "Detection of Mycobacterium tuberculosis DNA With Thermophilic Strand Displacement Amplification and Fluorescence Polarization," Clin. Chem. 42(10): 1604-1608, 1996.

Walker, "Empirical Aspects of Strand Displacement Amplification," PCR Methods and Applic. 3:1-6, 1993.

Walker et al., "Isothermal in Vitro Amplification of DNA by a Restriction Enzyme/DNA Polymerase System," PNAS USA 89:392-396, Jan. 1992.

Walker et al., "Multiplex Strand Displacement Amplification (SDA) and Detection of DNA Sequences from Mycobacterium tuberculosis and Other Mycobacteria," Nucl. Acids Res. 22(13):2670-2677, 1994.

Walker et al., "Strand Displacement Amplification-An Isothermal, in Vitro DNA Amplification Technique," Nucl. Acids Res. 20(7):1691-1696, 1992.

Walker et al., "Strand Displacement Amplification (SDA) and Transient-State Fluorescence Polarization Detection of Mycobacterium tuberculosis DNA," Clin. Chem. 42(1):9-13, 1996.

Walter et al., "Strand Displacement Amplification as an in Vitro Model for Rolling-Circle Replication: Deletion Formation and Evolution During Serial Transfer," PNAS USA 91:7937-7941, Aug. 1994.

Walter, Nils, "Modelling Viral Evolution in Vitro Using Exo Klenow Polymerase: Continuous Selection of Strand Displacement Amplified DNA that Binds an Oligodeoxynucleotide to Form a Triplehelix," J. Mol. Biol. 254:856-868, 1995.

Westin et al., "Antimicrobial Resistance and Bacterial Identification Utilizing a Microelectronic Chip Array," J. Clin. Microbiol. 39(3):1097-1104, Mar. 2001.

Westin et al., "Anchored Multiplex Amplification on a Microelectronic Chip Array," Nat. Biotech. 18:199-204, Feb. 2000.

Xu et al., "Engineering a Nicking Endonuclease N.AlwI by Domain Swapping," PNAS USA 98(23):12990-12995, Nov. 6, 2001.

Zhang et al., "Detection of Rare DNA Targets by Isothermal Ramification Amplification," Gene 274:209-216, 2001.

Zhang et al., "Detection of Chlamydia trachomatis by Isothermal Ramification Amplification Method: a Feasibility Study," J. Clin. Microbiol. 40(1):128-132, Jan. 2002.

Zwadyk et al., "Rendering of Mycobacteria Safe for Molecular Diagnostic Studies and Development of a Lysis Method for Strand Displacement Amplification and PCR," J. Clin. Microbiol. 32(9):2140-2146, Sep. 1994.

Barrett et al., "Genotypic analysis of multiple loci in somatic cells by whole genome amplification," Nucleic Acids Research 23(17):3488-3492, 1995.

Brown, "Genome scanning methods," Current Opinion in Genetics & Development 4:366-373, 1994.

Cheung and Nelson, "Whole genome amplification using a degenerate oligonucleotide primer allows hundreds of genotypes to be performed on less than one nanogram of genomic DNA," PNAS U.S.A 93:14676-14679, Dec. 1996.

Hahn et al., "Current Applications of single-cell PCR," Cellular and Molecular Life Sciences 57:96-105, 2000.

Klein et al., "Comparative genomic hybridization, loss of heterozygosity, and DNA sequence analysis of single cells," PNAS U.S.A. 96:4494-4499, Apr. 1999.

Zhang et al., "Whole genome amplification from a single cell: implications for genetic analysis," PNAS U.S.A. 89:5847-5851, Jul. 1992.

* cited by examiner

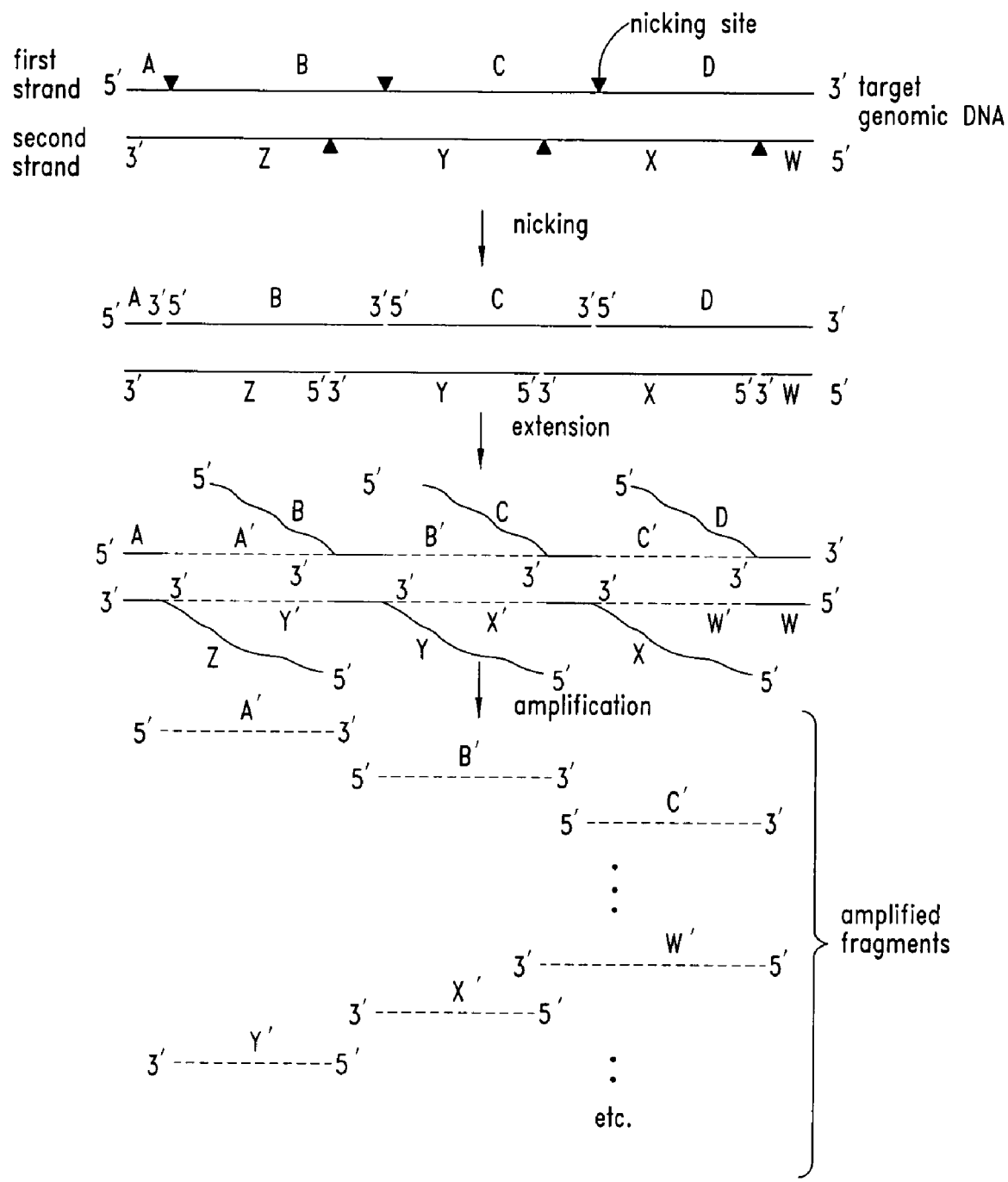

NUCLEIC ACID AMPLIFICATION USING NICKING AGENTS

BACKGROUND OF THE INVENTION

1. Field of the Invention

This invention relates to the field of molecular biology, more particularly to methods and compositions involving nucleic acids, and still more particularly to methods and compositions for amplifying nucleic acids, e.g., genomic DNA, using nicking agents.

2. Description of the Related Art

A number of methods have been developed for whole genome amplification. Most of these methods involve the use of random or partially random primers to amplify the entire genome of an organism in a PCR reaction (see, e.g., Kuukasjarvi et al., Genes, Chromosomes and Cancer 18: 94–101 (1997); Telenius et al., Genomics 13: 718–25, 1992; Zhang et al., Proc. Natl. Acad. Sc. USA 89: 5847–51, 1992; Cheung et al., Proc. Natl. Acad. Sci. 93: 14676–79, 1996; Barrett et al., Nucleic Acids Res. 23: 3488–92; Klein et al., Proc. Natl. Acad. Sci. USA 96: 4494–9, 1999; Sun et al., Nucleic Acids Res. 23: 3034–40, 1995; Larsen et al., Cytometry 44: 317–325, 2001; and Barbaux et al., J. Mol. Med. 79: 329–32, 2001). This technique relies on having a sufficient number of primers of random or partially random sequences so that pairs of primers hybridize throughout the genomic DNA at moderate intervals. Extension from the 3' termini of the primers produces strands to which another primer anneals. By subjecting the genomic DNA to multiple amplification cycles, the genomic sequences are amplified. Since this technique relies on PCR, it has the disadvantage that the amplification reaction must be carried out under cycles of different temperatures to achieve cycles of denaturation and re-annealing. Such cycles of denaturation and re-annealing are disadvantageous for many reasons, e.g., they may cause gene shuffling artifacts.

An alternative method for whole genome amplification is known as whole genome strand displacement amplification. This technique involves hybridization of random or partially random primers to a target genomic DNA and replication of the target sequence primed by the hybridized primers so that replication of the target sequence results in replicated strands complementary to the target sequence (see, e.g., U.S. Pat. Nos. 6,124,120 and 6,280,949). During replication, the growing replicated strands displace other replicated strands from the target sequence (or from another replicated strand) via strand displacement replication. Displacement of replicated strands by other replicated strands allows the amplification of a target sequence or portions thereof. Although this technique may be carried out under an isothermal condition, it requires the use of multiple primers.

There is a long felt need in the art for a simpler and more efficient method to amplify a whole genome. The present invention fulfills this and related needs as described below. In contrast to previously known techniques for whole genome amplification, the present invention provides a method for nucleic acid amplification that does not require the use of an external oligonucleotide primer. In addition, the present invention can be carried out under an isothermal condition, in other words isothermally, thus avoiding the expenses associated with the equipment for providing cycles of different temperatures and potential re-annealing or gene shuffling artifacts.

BRIEF SUMMARY OF THE INVENTION

In one aspect, the present invention provides a method for nucleic acid amplification comprising forming a mixture of (a) a double-stranded target nucleic acid composed of at least one strand having two or more nicking sites; (b) a nicking agent capable of selectively nicking at the two or more nicking sites; and (c) a DNA polymerase, under conditions allowing for the amplification of the target nucleic acid, wherein the amplification does not require the presence of an external oligonucleotide primer (ODNP) that is capable of annealing to a portion of the target nucleic acid. In certain embodiments, the amplification is performed in the absence of an external ODNP. The target nucleic acid is, in one aspect of the invention, genomic DNA.

In a related aspect, the present invention provides a method for nucleic acid amplification comprising (a) multiply nicking at least one strand of a double-stranded target nucleic acid with a nicking agent to provide at least two new 3' termini; (b) extending one or more of the at least two new 3' termini with a DNA polymerase to provide one or more extension products; (c) nicking one or more of the extension product(s) of step (b) to provide one or more nicked product; and (d) extending the nicked product of step (c) to thereby amplify at least a portion of the target nucleic acid.

In both of the aforementioned aspects, the double-stranded target nucleic acid may be derived, or prepared, from a single-stranded nucleic acid. The target nucleic acid, or single-stranded precursor thereof, may be isolated from any organism, organ, tissue or cell. For example, the nucleic acid may be isolated from a single cell such as a sperm cell or an oocyte. Other exemplary tissues and cells include, but are not limited to, buccal cells, blood and bone marrow. For instance, the organism from which the nucleic acid is isolated may be prokaryotic or eukaryotic, including but not limited to viruses, bacteria, yeast, higher plants, insects, mammals and humans. The nucleic acid may be isolated from a subject with, or suspected to have, a genetic disease. In a preferred method, the nucleic acid to be amplified is a genomic DNA such as a whole genome of an organism.

In a preferred embodiment, both strands of the double-stranded target nucleic acid molecule contain two or more nicking sites. In certain embodiments, the target nucleic acid may be immobilized to a solid support.

A nicking agent useful in the present methods may be, without limitation, a nicking endonuclease, such as N.BstNB I, N.Alw I, N.BbvC I-a, and N.BbvC I-b.

Preferably, a DNA polymerase useful in the present invention is a 5'→3' exonuclease deficient DNA polymerase, including but not limited to, exo⁻ Vent, exo⁻ Deep Vent, exo⁻ Bst, exo⁻ Pfu, exo⁻ Bca, the Klenow fragment of DNA polymerase I, T5 DNA polymerase, Phi29 DNA polymerase, phage M2 DNA polymerase, phage PhiPRD1 DNA polymerase, Sequenase, PRD1 DNA polymerase, 9°Nm™ DNA polymerase, or T4 DNA polymerase homoenzyme. In certain preferred embodiments, the 5'→3' exonuclease deficient DNA polymerase is exo⁻ Bst polymerase, exo⁻ Bca polymerase, exo⁻ Vent polymerase, 9° Nm™ DNA polymerase or exo⁻ Deep Vent polymerase. Preferably, the 5'→3' exonuclease deficient DNA polymerase has a strand displacement activity.

The present methods may be performed isothermally, for example, at a temperature within the range of 50° C.–70° C., preferably at about 55° C. In certain preferred embodiments, the amplification is performed in the presence of a strand displacement facilitator. Exemplary strand displacement facilitators include, but are not limited to, BMRF1 polymerase accessory subunit, adenovirus DNA-binding protein, herpes simplex viral protein ICP8, single-stranded DNA binding proteins, phage T4 gene 32 protein, calf thymus helicase, and trehalose. In certain preferred embodiments, the stand displacement facilitator is trehalose or phage T4 gene 32 protein.

In another aspect, the present invention provides a kit for genomic DNA amplification that does not require the use of an external oligonucleotide primer. The kit includes a nicking agent, a 5'→3' exonuclease deficient DNA polymerase, and preferably includes instructions for using the kit. The nicking agent present in the kit may be a nicking endonuclease, such as N.BstNB I. The 5'→3' exonuclease deficient DNA polymerase may be exo⁻ Vent, exo⁻ Deep Vent, exo⁻ Bst, exo⁻ Pfu, exo⁻ Bca, the Klenow fragment of DNA polymerase I, T5 DNA polymerase, Phi29 DNA polymerase, phage M2 DNA polymerase, phage PhiPRD1 DNA polymerase, Sequenase, PRD1 DNA polymerase, 9°Nm™ DNA polymerase, or T4 DNA polymerase homoenzyme. In a preferred embodiment, the kit includes a 5'→3' exonuclease deficient DNA polymerase selected from exo⁻ Bst polymerase, exo⁻ Bca polymerase, exo⁻ Vent polymerase, 9°Nm™ DNA polymerase, and exo⁻ Deep Vent polymerase. Preferably, the 5'→3' exonuclease deficient DNA polymerase has a strand displacement activity.

The kit of the present invention may include a buffer for the nicking agent and/or a buffer for the 5'→3' exonuclease deficient DNA polymerase. In one aspect of the invention, the kit includes a buffer suitable for both the nicking agent and the DNA polymerase. The kit of the present invention may include a strand displacement facilitator, such as BMRF1 polymerase accessory subunit, adenovirus DNA-binding protein, herpes simplex viral protein ICP8, single-stranded DNA binding proteins, phage T4 gene 32 protein, calf thymus helicase or trehalose. In a preferred embodiment, the kit includes a strand displacement facilitator selected from trehalose and phage T4 gene 32 protein.

In certain preferred embodiments, the kit of the present invention is especially useful for whole genome amplification. In those embodiments, the instructions for using the kit comprise information about how to use the kit for amplifying a whole genome of an organism.

In another aspect, the present invention provides a method for whole genome amplification comprising (a) nicking a whole genome with a nicking agent to provide nicked product; and (b) amplifying at least a portion of the whole genome using a nicking product of step (a) as a template. Step (b) of the method may be performed by a polymerase chain reaction using a random primer, a partially random primer, or a specific primer. Alternatively, whole genome amplification may be performed in the absence of any external oligonucleotide primers (ODNPs). The whole genome (also referred to as "target genome") may be isolated from any organism, organ, tissue or cell. For example, the target genome may be isolated from a single cell such as a sperm cell or an oocyte. Other exemplary tissues and cells include, but are not limited to, buccal cells, blood and bone marrow. The organism from which the target genome is isolated may be prokaryotic or eukaryotic, including but not limited to viruses, bacteria, yeast, higher plants, insects, mammals and humans. The target genome may be isolated from a subject with, or suspected to have, a genetic disease.

A nicking agent useful in the method for whole genome amplification may be, without limitation, a nicking endonuclease, such as N.BstNB I. The DNA polymerase useful in whole genome amplification may or may not be 5'→3' exonuclease deficient. Exemplary 5'→3' exonuclease deficient DNA polymerases, include, without limitation, exo⁻ Vent, exo⁻ Deep Vent, exo⁻ Bst, exo⁻ Pfu, exo⁻ Bca, the Klenow fragment of DNA polymerase I, T5 DNA polymerase, Phi29 DNA polymerase, phage M2 DNA polymerase, phage PhiPRD1 DNA polymerase, Sequenase, PRD1 DNA polymerase, 9°Nm™ DNA polymerase, or T4 DNA polymerase homoenzyme. In certain preferred embodiments, the 5'→3'exonuclease deficient DNA polymerase is exo⁻ Bst polymerase, exo⁻ Bca polymerase, exo⁻ Vent polymerase or exo⁻ Deep Vent polymerase. In a preferred embodiment, the 5'→3' exonuclease deficient DNA polymerase has a strand displacement activity.

The method for whole genome amplification may be performed isothermally, for example, at a temperature within the range of about 50° C.–70° C., preferably at about 55° C. In certain preferred embodiments, the amplification is performed in the presence of a strand displacement facilitator. Exemplary strand displacement facilitators include, but are not limited to, BMRF1 polymerase accessory subunit, adenovirus DNA-binding protein, herpes simplex viral protein ICP8, single-stranded DNA binding proteins, phage T4 gene 32 protein, calf thymus helicase, and trehalose. In certain preferred embodiments, the stand displacement facilitator is trehalose or phage T4 gene 32 protein.

These and other aspects of the present invention will become evident upon reference to the following detailed description and attached drawing. Various references identified herein are incorporated by reference in their entireties.

BRIEF DESCRIPTION OF THE DRAWING

The attached FIGURE is a schematic diagram of the major steps of an exemplary method for nucleic acid amplification according to the present invention. Solid lines represent portions of a target genomic DNA, while gapped lines represent extension or amplification products.

DETAILED DESCRIPTION OF THE INVENTION

The present invention provides simple and efficient methods and kits for amplifying target nucleic acids using nicking agents. In certain embodiments, the amplification does not require the presence of any external oligonucleotide primers that are capable of annealing to a portion of the target nucleic acid. These methods and kits are useful in many areas, including, to name a few, genetic disease diagnosis, forensics, paleoarcheology, genetic linkage analysis, and genetic diversity studies.

A. Conventions/Definitions

Prior to providing a more detailed description of the present invention, it may be helpful to an understanding thereof to define conventions and provide definitions as used herein, as follows. The terms "3'" and "5'" are used herein to describe the location of a particular site within a single strand of nucleic acid. When a location in a nucleic acid is "3' to" or "3' of" a nucleotide reference or string of nucleotides, this means that the location is between the reference nucleotide(s) and the 3 hydroxyl of that strand of nucleic acid. Likewise, when a location in a nucleic acid is "5' to" or "5' of" a reference nucleotide, this means that it is between the reference nucleotide and the 5' phosphate of that strand of nucleic acid.

The term "nicking," as used herein, refers to the cleavage of only one strand of the double-stranded portion of a fully or partially double-stranded nucleic acid. The position where the nucleic acid is nicked is referred to as the "nicking site" (NS). A "nicking agent" (NA) is an agent that nicks a partially or fully double-stranded nucleic acid. It may be an enzyme or any other chemical compound or composition. In certain embodiments, a nicking agent may recognize a particular nucleotide sequence of a fully or partially double-stranded nucleic acid and cleaves only one strand of the fully or partially double-stranded nucleic acid at a specific position (i.e., the NS) relative to the location of the recognition sequence. Such nicking agents (referred to as "specific nicking agents" include, but are not limited to, a nicking endonuclease (e.g., N.BstNB I), and a restriction endonuclease (e.g., Hinc II) when the fully or partially double-stranded DNA contains a hemimodified recognition/cleavage site in which one strand contains at least one derivatized nucleotide that prevents cleavage of one strand (i.e., the strand that contains the derivatized nucleotide or the other strand that does not contain the derivatized nucleotide) by the restriction endonuclease.

A "nicking endonuclease" (NE), as used herein, refers to an endonuclease that recognizes a nucleotide sequence of a completely or partially double-stranded nucleic acid molecule and cleaves only one strand of the nucleic acid molecule at a specific location relative to the recognition sequence. Unlike a restriction endonuclease (RE), which requires its recognition sequence to be modified by containing at least one derivatized nucleotide to prevent cleavage of the derivatized nucleotide-containing strand of a fully or partially double-stranded nucleic acid molecule, a NE typically recognizes a nucleotide sequence composed of only native nucleotides and cleaves only one strand of a fully or partially double-stranded nucleic acid molecule that contains the nucleotide sequence.

As used herein, "native nucleotide" refers to adenylic acid, guanylic acid, cytidylic acid, thymidylic acid or uridylic acid. A "derivatized nucleotide" is a nucleotide other than a native nucleotide.

The nucleotide sequence of a completely or partially double-stranded nucleic acid molecule that a NA recognizes is referred to as the "nicking agent recognition sequence" (NARS). Likewise, the nucleotide sequence of a completely or partially double-stranded nucleic acid molecule that a NE recognizes is referred to as the "nicking endonuclease recognition sequence" (NERS). The specific sequence that a RE recognizes is referred to as the "restriction endonuclease recognition sequence" (RERS). A "hemimodified RERS," as used herein, refers to a double-stranded RERS in which one strand of the recognition sequence contains at least one derivatized nucleotide (e.g., a-thio deoxynucleotide) that prevents cleavage of that strand (i.e., the strand that contains the derivatized nucleotide within the recognition sequence) by a RE that recognizes the RERS.

In certain embodiments, a NARS is a double-stranded nucleotide sequence where each nucleotide in one strand of the sequence is complementary to the nucleotide at its corresponding position in the other strand. In such embodiments, the sequence of a NARS in the strand containing a NS nickable by a NA that recognizes the NARS is referred to as a "sequence of the sense strand of the NARS" or a "sequence of the sense strand of the double-stranded NARS," while the sequence of the NARS in the strand that does not contain the NS is referred to as a "sequence of the antisense strand of the NARS" or a "sequence of the antisense strand of the double-stranded NARS."

Likewise, in the embodiments where a NERS is a double-stranded nucleotide sequence of which one strand is exactly complementary to the other strand, the sequence of a NERS located in the strand containing a NS nickable by a NE that recognizes the NERS is referred to as a "sequence of a sense strand of the NERS" or a "sequence of the sense strand of the double-stranded NERS," while the sequence of the NERS located in the strand that does not contain the NS is referred to a "sequence of the antisense strand of the NERS" or a "sequence of the antisense strand of the double-stranded NERS." For example, the recognition sequence and the nicking site of an exemplary nicking endonuclease, N.BstNB I, are shown below with "▼" to indicate the cleavage site and N to indicate any nucleotide:

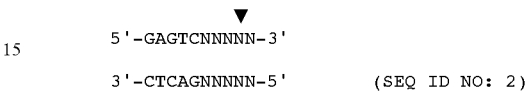

```
        ▼
5'-GAGTCNNNNN-3'

3'-CTCAGNNNNN-5'          (SEQ ID NO: 2)
```

The sequence of the sense strand of the N.BstNB I recognition sequence is 5'-GAGTC-3', whereas that of the antisense strand is 5'-GACTC-3'.

Similarly, the sequence of a hemimodified RERS in the strand containing a NS nickable by a RE that recognizes the hemimodified RERS (i.e., the strand that does not contain any derivatized nucleotides) is referred to as "the sequence of the sense strand of the hemimodified RERS" and is located in "the sense strand of the hemimodified RERS," while the sequence of the hemimodified RERS in the strand that does not contain the NS (i.e., the strand that contains derivatized nucleotide(s)) is referred to as "the sequence of the antisense strand of the hemimodified RERS" and is located in "the antisense strand of the hemimodified RERS."

In certain other embodiments, a NARS is an at most partially double-stranded nucleotide sequence that has one or more nucleotide mismatches, but contains an intact sense strand of a double-stranded NARS as described above. According to the convention used herein, in the context of describing a NARS, when two nucleic acid molecules anneal to one another so as to form a hybridized product, and the hybridized product includes a NARS, and there is at least one mismatched base pair within the NARS of the hybridized product, then this NARS is considered to be only partially double-stranded. Such NARSs may be recognized by certain nicking agents (e.g., N.BstNB I) that require only one strand of double-stranded recognition sequences for their nicking activities. For instance, the NARS of N.BstNB I may contain, in certain embodiments, an intact sense strand, as follows,

```
5'-GAGTC-3'

3'-NNNNN-5'
``` where N indicates any nucleotide, and N at one position may or may not be identical to N at another position, however there is at least one mismatched base pair within this recognition sequence. In this situation, the NARS will be characterized as having at least one mismatched nucleotide.

In certain other embodiments, a NARS is a partially or completely single-stranded nucleotide sequence that has one or more unmatched nucleotides, but contains an intact sense strand of a double-stranded NARS as described above. According to the convention used herein, in the context of describing a NARS, when two nucleic acid molecules (i.e., a first and a second strand) anneal to one another so as to form a hybridized product, and the hybridized product includes a nucleotide sequence in the first strand that is recognized by a NA, i.e., the hybridized product contains a NARS, and at least one nucleotide in the sequence recognized by the NA does not correspond to, i.e., is not across from, a nucleotide in the second strand when the hybridized product is formed, then there is at least one unmatched nucleotide within the NARS of the hybridized product, and this NARS is considered to be partially or completely single-stranded. Such NARSs may be recognized by certain nicking agents (e.g., N.BstNB I) that require only one strand of double-stranded recognition sequences for their nicking activities. For instance, the NARS of N.BstNB I may contain, in certain embodiments, an intact sense strand, as follows,

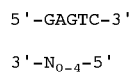

(where "N" indicates any nucleotide, 0–4 indicates the number of the nucleotides "N," a "N" at one position may or may not be identical to a "N" at another position), which contains the sequence of the sense strand of the double-stranded recognition sequence of N.BstNB I. In this instance, at least one of G, A, G, T or C is unmatched, in that there is no corresponding nucleotide in the complementary strand. This situation arises, e.g., when there is a "loop" in the hybridized product, and particularly when the sense sequence is present, completely or in part, within a loop.

In some embodiments of the present invention, a nicking agent may be an agent that does not require a specific recognition sequence in a double-stranded target nucleic acid and creates one or more randomly placed nicks in the target. Such a nicking agent is referred to as a "random nicking agent" and may be an enzyme or any other chemical compound or composition.

As used herein, a nucleotide in one strand (referred to as the "first strand") of a double-stranded nucleic acid located at a position "corresponding to" another position (e.g., a defined position) in the other strand (referred to as the "second strand") of the double-stranded nucleic acid refers to the nucleotide in the first strand that is complementary to the nucleotide at the corresponding position in the second strand. Likewise, a position in one strand (referred to as the "first strand") of a double-stranded nucleic acid corresponding to a nicking site within the other strand (referred to as the "second strand") of the double-stranded nucleic acid refers to the position between the two nucleotides in the first strand complementary to those in the second strand that surround the nicking site.

As used herein, the phrase "amplification of at least a portion of a double-stranded target nucleic acid" refers to the making of one, two, three or more copies of a nucleic acid molecule (either single-stranded, e.g., produced via strand displacement amplification; or double-stranded, e.g., produced via polymerase chain reaction) by a DNA polymerase using one strand, both strands of a double-stranded target nucleic acid molecule (or multiple target nucleic acid molecules with identical sequences), or a portion of one strand or both strands as a template (or templates). The newly made nucleic acid molecules must comprise a nucleotide sequence identical to at least a portion of the target nucleic acid. However, the above phrase does not include a strand replacement of a portion of a target nucleic acid where a new segment of nucleic acid that is identical to a portion of one strand of the target nucleic acid is made while the corresponding portion of that strand of the target nucleic acid is degraded. In other words, the above phrase does not include a strand replacement where the end result is that a newly synthesized portion of a strand replaces the corresponding original portion of the strand in a target nucleic acid and no additional nucleic acid molecule (i.e., a displaced nucleic acid fragment) is produced.

As used herein, "whole genome" (or "target genome") refers to at least 80% of the total set of genes and nucleic acid sequences between these genes carried by an organism, a cell or an organelle. For a genome composed of a single-stranded DNA, a single-stranded RNA or a double-stranded RNA, a double-stranded DNA may be prepared using the single-stranded DNA, the single-stranded RNA or the double-stranded RNA as a template. The resulting double-stranded DNA may then be used as a template for whole genome amplification according to the present invention and is also included by the term "whole genome" or "target genome" as used herein.

As used herein, "whole genome amplification" refers to the making of multiple nucleic acid molecules (either single-stranded, e.g., produced via strand displacement amplification; or double-stranded, e.g., produced via polymerase chain reaction) using one strand, both strands of a double-stranded target genome, or a portion of one strand or both strands as a template. These nucleic acid molecules each must comprise a nucleotide sequence identical to a portion of the target genome. Typically, these nucleic acid molecules, in combination, comprise the majority portion of the sequence (i.e., at least 51%) of the target genome. Preferably, such nucleic acid molecules, in combination, comprise 60%, 70%, 80%, 90%, 95%, or 100% of the target genome.

B. Methods for Nucleic Acid Amplification That do not Require an External Primer In one aspect, the present invention provides methods for amplifying a target nucleic acid that do not require the use of an external oligonucleotide primer (ODNP). The target nucleic acid (also referred to as "template nucleic acid") comprises at least two nicking sites in one strand of the target nucleic acid. Such a target nucleic acid is nicked in the presence of a NA capable of cleaving at the nicking sites. The resulting 3' terminus at the NS is then extended by a DNA polymerase, preferably being 5'→3' exonuclease deficient and having a strand displacement activity and/or in the presence of a strand displacement facilitator, displacing the strand that contains the 5' terminus produced by the nicking reaction. The resulting extension product having either a recreated NARS for a specific NA or a random NS for a random NA is nicked ("re-nicked") by the specific NA or the random NA. The 3' terminus produced at the NS by the re-nicking is then extended in the presence of the DNA polymerase, also displacing the strand that contains the 5' terminus produced by the nicking reaction. The nicking-extension cycle is repeated, preferably multiple times, to accumulate/amplify the displaced strand that contains the 5' terminus produced by the nicking reaction.

In certain preferred embodiments, the present method may be used for whole genome amplification. The major steps of these embodiments are illustrated in the attached FIGURE. For simplicity, only a portion of a whole genome (referred to as "target genome" or "template genome") is shown: Regions A, B, C and D in the first strand and Regions W, X, Y and Z in the second strand. Regions A, B, C, and D are delineated by the NSs between the neighboring regions in the first strand. Likewise, Regions W, X, Y and Z are delineated by the NSs between the neighboring regions in the second strand. Also for simplicity, the NSs shown in the attached FIGURE are potential NSs of a specific NA. However, one of ordinary skill in the art understands similar procedures of the present methods where a random NA is used in view of the description provided herein.

Referring to the attached drawing, in the presence of a specific NA that recognizes the NARSs present in both strands of the target genome, the target genome is nicked at various NSs. The resulting 3' terminus at each nicking site in both strands (e.g., the NS between Regions A and B, referred to as "NS:A-B"; the NS between Regions B and C, referred to as "NS:B-C"; etc.) is then extended by action of a 5'→3' exonuclease deficient DNA polymerase using complementary strands as a template. The extension is typically terminated at the first position corresponding to a NS in the template strand (i.e., the complementary strand of the extending strand). The extended strand displaces the portion of the strand of the target nucleic acid that was complementary to the template strand if the DNA polymerase has a strand displacement activity and/or if a strand displacement facilitator is present in the reaction mixture. For instance, the 3' terminus at the nicking site NS:A-B (i.e., the 3' terminus of Region A after the target nucleic acid has been nicked) is extended using Region Z as a template in the presence of a 5'→3' exonuclease deficient DNA polymerase. The extension by the DNA polymerase will be terminated at the position corresponding to the nicking site NS:Y-Z assuming nicking has occurred at NS:Y-Z. The extended strand (represented by a gapped line and denoted as "Region A'" in the attached drawing) displaces a portion of Region B. However, as the 3' portion of Region B still anneals to its complementary strand, the 3' terminus of Region B can still be extended by the DNA polymerase. Likewise, the 3' terminus at the nicking site NS:Y-Z (i.e., the 3' terminus of Region Y after the target nucleic acid is nicked) is extended using Region B as a template in the presence of the 5'→3' exonuclease deficient DNA polymerase. The extension is terminated at the position corresponding to the nicking site NS:A-B (i.e., the 3' terminus of Region A after the target nucleic acid is nicked). The extended strand (represented by a gapped line and denoted as "Region Y'" in the attached drawing) displaces a portion of Region Z. However, as the 3' portion of Region Z still anneals to its complementary strand, the 3' terminus of Region Z can still be extended by the DNA polymerase.

The extension of the 3' terminus at each nicking site reproduces the NS that the NA is able to nick, allowing for and resulting in the nicking ("re-nicking") of the extension product. The 3' terminus reproduced by the re-nicking is then extended ("re-extended") by the DNA polymerase, displacing the strand that annealed to the template target nucleic acid (i.e., the portion of nucleic acid that was extended during the initial extension). For instance, the extension product from the 3' terminus of Region A during the first round of extension (i.e., the nucleic acid fragment consisting of Regions A and A') can be re-nicked by the NA, producing a free 3' terminus of Region A for another round of extension by the DNA polymerase. The second round of extension displaces Region A' produced during the initial round of extension. The nicking and extension cycle is repeated automatically multiple times, resulting in the accumulation/amplification of Region A'. Similarly, the other extended sequences produced during the initial round of extension (e.g., Regions B', C', W', X', Y') are also amplified.

In certain circumstances, besides Regions A', B', C', W', X' and Y', additional, longer fragments may also be produced/amplified. For instance, not all of the potential nicking sites are nicked under certain conditions (e.g., the amount of a nicking agent in a reaction mixture is less than that required for complete nicking of a target nucleic acid). Assuming that the potential nicking site NS:Y-Z in the second strand of the target nucleic acid or in an extension product comprising Regions Y and Y' has not been nicked by the nicking agent present in the nicking-extension reaction mixture, extension from the 3' terminus of Region A will continue beyond Region A', using Region Y as a template. Thus, a molecule consisting of Regions A, B and B' is synthesized/amplified if the nicking site NS:X-Y has been nicked. However, in the absence of the nicking at the nicking site NS:X-Y in the target nucleic acid molecule or in an extension product thereof, the extension from 3' terminus of Region A may continue further until the DNA polymerase catalyzing the extension reaches a nicked site in its template strand (i.e., the second strand of the target nucleic acid, or an extension product initialed from a 3' terminus of a region in the second strand of the target).

As will be discussed in detail below, in certain embodiments, the nicking agent is a nicking endonuclease (e.g., N.BstNB I). N.BstNB I recognizes the sequence 5'-GAGTC-3' and nicks at four nucleotides 3' to the "C" of the recognition sequence. On average, this recognition sequence occurs every 3,000 to 5,000 nucleotides in both strands of naturally occurring DNA (e.g., genomic sequences). Since the recognition site for the endonuclease is typically randomly distributed in naturally occurring DNA, the amplification products of the above-described nicking-extension reaction are faithful representations of the composition of the starting materials (i.e., the naturally occurring DNA used as the template during nucleic acid amplification).

As discussed above, the present invention provides a method for amplifying a double-stranded target nucleic acid (including a whole genome) that does not require the presence of an external oligonucleotide primer (ODNP). An "external ODNP," as used herein, refers to an ODNP that is added to the nicking-extension reaction mixture and functions as a primer for extending from the 3' terminus of the primer using one strand of the target nucleic acid as a template by a DNA polymerase. Such an external ODNP comprises a sequence that is either completely or substantially complementary to a portion of one strand of the target nucleic acid so that it is capable of specific annealing to a portion of the target nucleic acid. Because the 3' terminus produced by the nicking of an NA in the target nucleic acid may be extended by a DNA polymerase, the portion of the strand of the target nucleic acid having the 3' terminus at the nicking site produced by the NA functions as an internal primer for the extension by the DNA polymerase. Thus, the method of the present invention does not require the presence of an external ODNP for the amplification of portions of the target nucleic acid. However, the present invention includes methods of nucleic acid amplification wherein an additional ODNP is used in the reaction mixture for other purposes.

1. Target Nucleic Acids

The target nucleic acid of the present invention is any double-stranded nucleic acid molecule that comprises a nicking agent recognition sequence. It may be derived, or prepared, from a single-stranded nucleic acid molecule. The techniques for synthesizing double-stranded nucleic acid molecules from single-stranded nucleic acid molecules are well known (see generally, Sambrook and Russell, Molecular Cloning: A Laboratory Manual, 2001).

Preferably, the target nucleic acid is naturally occurring, as in genomic DNAs. More preferably, the target nucleic acid is a whole genome of an organism of interest, including but not limited to, bacteria, yeast, higher plants, insects, and mammals (especially humans).

In certain embodiments, the target nucleic acid need not be first isolated before being used as a template for nucleic acid amplification. In other words, nucleic acid amplification may be performed in situ, i.e., in the tissue(s) or cell(s) a target nucleic acid is present. Alternatively, the target nucleic acid may be first at least partially purified before functioning as a template.

Methodology for isolating populations of nucleic acids from biological samples is well known and readily available to those skilled in the art of the present invention. Exemplary techniques are described, for example, in Sambrook and Russell, supra and Ausubel et al., "Short Protocols in Molecular Biology." Nucleic acid isolation kits are also commercially available from numerous companies, and may be used to simplify and accelerate the isolation process.

The target nucleic acids may be isolated from a whole organism, an organ, a tissue (e.g., a tumor tissue), body fluid (e.g., blood and bone marrow), or a single cell (e.g., a sperm or an oocyte). In certain preferred embodiments, the target nucleic acids are isolated from tissue of a subject with, or suspected to have, a disease, especially a genetic disease (e.g., Down's syndrome).

In certain embodiments, the target nucleic acid may be immobilized to a solid support. Methods for immobilizing nucleic acid in known in the art, including without limitation, the use of a fixative, Southern blotting, and transferring target nucleic acid onto a substrate that binds to a nucleic acid, such as nitrocellulose, nylon, and poly(ethyleneimine)-coated metal.

In certain embodiments, the target nucleic acid may be derived from a naturally occurring nucleic acid. The term "derived from," as used herein, refers to a process whereby an original nucleic acid is manipulated, for example, to insert/create a specific nicking site.

2. Nicking Agents

The target nucleic acid of interest can be nicked by any nicking agent that cleaves/nicks only one strand of a double-stranded nucleic acid molecule. In certain embodiments, the nicking agent may recognize a nicking agent recognition sequence (NARS) in the target nucleic acid and is referred to as a "specific nicking agent." Preferably, a specific nicking agent is an enzyme that recognizes a specific sequence of a double-stranded nucleic acid and cleaves only one strand of the nucleic acid. Such an enzyme can be, for example, a nicking endonuclease that recognizes a specific sequence that consists of native nucleotides, or a restriction endonuclease that recognizes a hemimodified recognition sequence. While nicking agents may and typically will create nicks in both strands of a double stranded target, a nick created in one strand is, in no way, related to a nick created in the other strand. A preferred nicking agent is a specific nicking agent, and a preferred specific nicking agent is a nicking endonuclease.

A nicking endonuclease may or may not have a nicking site that overlaps with its recognition sequence. An exemplary NE that nicks outside its recognition sequence is N.BstNB I, which recognizes a unique nucleic acid sequence composed of 5'-GAGTC-3', but nicks four nucleotides beyond the 3' terminus of the recognition sequence. The recognition sequence and the nicking site of N.BstNB I are shown below with "▼" to indicate the cleavage site where the letter N denotes any nucleotide:

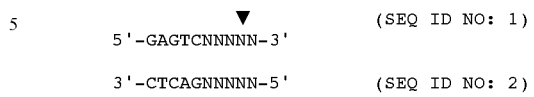

N.BstNB I may be prepared and isolated as described in U.S. Pat. No. 6,191,267. Buffers and conditions for using this nicking endonuclease are also described in the '267 patent. An additional exemplary NE that nicks outside its recognition sequence is N.AlwI, which recognizes the following double-stranded recognition sequence:

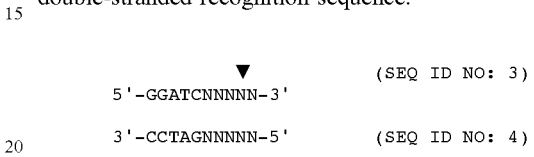

The nicking site of N.AlwI is also indicated by the symbol "▼". Both NEs are available from New England Biolabs (NEB). N.AlwI may also be prepared by mutating a type IIs RE AlwI as described in Xu a at. (*Proc. Nad. Acad Sci. USA* 98:12990–5, 2001).

Exemplary NEs that nick within their NERSs include N.BbvCI-a and N.BbvCI-b. The recognition sequences for the two NEs and the NSs (indicated by the symbol "▼") are shown as follows:

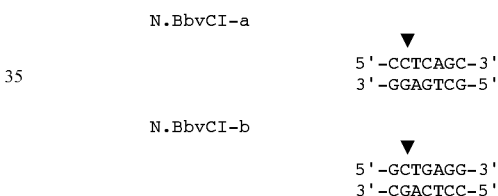

Both NEs are available from NEB.

Additional exemplary nicking endonucleases include, without limitation, N.BstSE I (Abdurashitov et al., *Mol. Biol.* (*Mosk*) 30: 1261–7, 1996), an engineered EcoR V (Stahl et al., *Proc. Natl. Acad. Sci. USA* 93: 6175–80, 1996), an engineered Fok I (Kim et al., *Gene* 203: 43–49, 1997), endonuclease V from *Thermotoga maritima* (Huang et al., *Biochem.* 40: 8738–48, 2001), Cvi Nickases (e.g., CviNY2A, CviNYSI, Megabase Research Products, Lincoln, Nebr.) (Zhang et al., *Virology* 240: 366–75, 1998; Nelson et al., *Biol. Chem.* 379: 423–8, 1998; Xia et al., *Nucleic Acids Res.* 16: 9477–87, 1988), and an engineered Mly I (i.e., N.Mly I) (Besnier and Kong, *EMBO Reports* 2: 782–6, 2001). Additional NEs may be obtained by engineering other restriction endonuclease, especially type IIs restriction endonucleases, using methods similar to those for engineering EcoR V, AlwI, Fok I and/or Mly I.

A RE useful as a nicking agent can be any RE that nicks a double-stranded nucleic acid at its hemimodified recognition sequences. Exemplary REs that nick their double-stranded hemimodified recognition sequences include, but are not limited to Ava I, Bsl I, BsmA I, BsoB I, Bsr I, BstN I, BstO I, Fnu4H I, Hinc II, Hind II and Nci I. Additional REs that nick a hemimodified recognition sequence may be screened by the strand protection assays described in U.S. Pat. No. 5,631,147.

REs that nick a hemimodified restriction endonuclease recognition sequence may be purchased from various companies such as, e.g., New England Biolabs Inc. (Beverly, Mass.; www.neb.com); Stratagene (La Jolla, Calif.; www-.stratagene.com), Promega (Madison, Wis.: www.promega-.com), and Clontech (Palo Alto, Calif.; www.clontech.com). Non-commercially available restriction enzymes may be isolated and/or purified based on the teaching available in the art. Conditions for using the restriction endonuclease for nicking a template nucleic acid may or may not be the same as those for cleaving a double-stranded nucleic acid. These conditions can be optimized for the nicking activities of the RE using ordinary skill in the art (see, e.g., Walker, *PCR Methods Appl.* 3:1–6, 1993, incorporated herein by reference in its entirety).

Additional specific nicking agents may include F1 gene product II or homologous enzymes from other filamentous bacteriophage, which nicks at the "origin of replication" from a filamentous bacteriophage such as fl or fd. In addition, uracil DNA glycosylase that removes uracil residues from nucleic acids and subsequently leaves an abasic site, which can be converted to a nick by various treatments, may also be used to create a specific nicking site. Furthermore, a specific nick in a double-stranded nucleic acid molecule may also be made by chemical methods such as that directed by triple-helix formation. A detailed description of these additional specific nicking agents may be found in U.S. Pat. No. 6,197,557, incorporated herein in its entirety.

Certain specific nicking agents require only the presence of the sense strand of a double-stranded recognition sequence in an at least partially double-stranded substrate nucleic acid for their nicking activities. For instance, N.BstNB I is active in nicking a substrate nucleic acid that comprises, in one strand, the sequence of the sense strand of its recognition sequence "5'-GAGTC-3'" of which one or more nucleotides do not form conventional base pairs (e.g., G:C, A:T, or A:U) with nucleotides in the other strand of the substrate nucleic acid. The nicking activity of N.BstNB I decreases with the increase of the number of the nucleotides in the sense strand of its recognition sequence that do not form conventional base pairs with any nucleotides in the other strand of the substrate nucleic acid. However, even none of the nucleotides of "5'-GAGTC-3'" form conventional base pairs with the nucleotides in the other strand, N.BstNB I may still retain 10–20% of its optimum activity.

In certain embodiments, a specific nicking agent may recognize a nucleotide sequence in a DNA-RNA duplex and nicks in one strand of the duplex. In certain other embodiments, a nicking agent may recognize a nucleotide sequence in a double-stranded RNA and nicks in on strand of the RNA.

In certain embodiments, a random nicking agent may be used to create one or more random nicking sites in a target nucleic acid molecule. Such a random nicking agent may be an enzyme or a chemical compound or a composition. A preferred enzymatic random nicking agent is DNAase I, which is commercially available. Additional enzymatic random nicking agents include certain restriction enzymes (e.g., CviJI, BamH I, EcoR I, EcoR V and Hinf I) that may function as random nicking agents under certain reaction conditions (e.g., high glycerol concentrations, high amounts of restriction enzyme and high pH). In addition, random nicks can also be produced using chemicals such as hydroxyl radicals. A detailed description of random nicking agents and methods may be found in U.S. Pat. No. 6,197,557.

Generally, the present method uses only one nicking agent in a particular nicking-extension reaction. However, in certain embodiments, multiple nicking agents may be used together in a nicking-extension reaction (i.e., a nucleic acid amplification reaction of the present invention). For instance, two specific nicking agents may be used in a single nicking-extension reaction to amplify nucleic acid fragments shorter than those from a reaction where only one specific nicking agent is present.

Depending on the desired length of an amplified nucleic acid molecule, the concentration of the nicking agent may be equal to, less than, or greater than, a saturation concentration under a given reaction condition. A "saturation concentration," as used herein, refers to the minimum concentration at which all the potential nicking sites of a target nucleic acid molecule are nicked. As one of ordinary skill in the art would appreciate, the lengths of the amplification products are likely to increase with a decrease in the concentration of a nicking agent in the reaction mixture: Lower concentrations of the nicking agent result in fewer nicks in the target nucleic acid or extension products thereof, which function as extension templates, allowing for longer nucleic acid extensions.

Accordingly, in the circumstances where relatively long amplification products are desirable, the concentration of a nicking agent in a reaction mixture may be between 0.1% to 99.9% of the saturation concentration.

In addition, the length of an amplified nucleic acid may also depend on the amount of DNA polymerase in a nicking-extension reaction mixture in certain circumstances. For instance, in a nicking-extension reaction that employs a random nicking agent (e.g., DNAase I), the presence of a relatively small amount of DNA polymerase may result in the amplification of relatively short nucleic acid fragments. With an increase in the number of DNA polymerase molecules in a nicking-extension reaction, the number of amplified nucleic acid molecules at a given time point will increase, providing a greater number of substrate molecules for the nicking agent. Such an increase in the number of substrates will occupy more nicking agent molecules, which would otherwise nick target nucleic acid molecules or extension products thereof at additional sites.

3. DNA Polymerases

The nicking of the target nucleic acid produces 3' termini at the nicking sites, from which extension may be performed in the presence of a DNA polymerase. When the DNA polymerase lacks a 5'→3' exonuclease activity, but has a strand displacement activity, the extension of the nicked template nucleic acid at the nicking site displaces the downstream single-stranded nucleic acid fragment. Such displacement allows the accumulation, thus amplification, of the single-stranded nucleic acid fragment.

Any DNA polymerase that is 5'→3' exonuclease deficient but has a strand displacement activity may be used to extend from a nicked template nucleic acid and to subsequently amplify a single-stranded nucleic acid in the continuous presence of a nicking agent. Such DNA polymerases include, but are not limited to, exo⁻ Deep Vent, exo⁻ Bst, exo⁻ Pfu, and exo⁻ Bca. Additional DNA polymerase useful in the present invention may be screened for or created by the methods described in U.S. Pat. No. 5,631,147, incorporated herein by reference in its entirety. The strand displacement activity may be further enhanced by the presence of a strand displacement facilitator as described below.

Alternatively, in certain embodiments, a DNA polymerase that does not have a strand displacement activity may be used. Such DNA polymerases include, but are not limited to, exo⁻ Vent, Taq, the Klenow fragment of DNA polymerase I, T5 DNA polymerase, and Phi29 DNA polymerase. In certain embodiments, the use of these DNA polymerases requires the presence of a strand displacement facilitator. A "strand displacement facilitator" is any compound or composition that facilitates strand displacement during nucleic acid extensions from a 3' terminus at a nicking site catalyzed by a DNA polymerase. Exemplary strand displacement facilitators useful in the present invention include, but are not limited to, BMRF1 polymerase accessory subunit (Tsurumi et al., *J. Virology* 67: 7648–53, 1993), adenovirus DNA-binding protein (Zijderveld and van der Vliet, *J. Virology* 68: 1158–64, 1994), herpes simplex viral protein ICP8 (Boehmer and Lehman, *J. Virology* 67: 711–5, 1993; Skaliter and Lehman, *Proc. Natl. Acad. Sci. USA* 91: 10665–9, 1994), single-stranded DNA binding protein (Rigler and Romano, *J. Biol. Chem.* 270: 8910–9, 1995), phage T4 gene 32 protein (Villemain and Giedroc, *Biochemistry* 35: 14395–4404, 1996), calf thymus helicase (Siegel et al., *J. Biol. Chem.* 267: 13629–35, 1992) and trehalose. In one embodiment, trehalose is present in the amplification reaction mixture.

Additional exemplary DNA polymerases useful in the present invention include, but are not limited to, phage M2 DNA polymerase (Matsumoto et al., *Gene* 84: 247, 1989), phage PhiPRD1 DNA polymerase (Jung et al., *Proc. Natl. Acad. Sci. USA* 84: 8287, 1987), T5 DNA polymerase (Chatterjee et al., *Gene* 97: 13–19, 1991), Sequenase (U.S. Biochemicals), PRD1 DNA polymerase (Zhu and Ito, *Biochim. Biophys. Acta.* 1219: 267–76, 1994), 9°N$_m$™ DNA polymerase (New England Biolabs) (Southworth et al., *Proc. Natl. Acad. Sci.* 93: 5281–5, 1996; Rodriquez et al., *J. Mol. Biol.* 302: 447–62, 2000), and T4 DNA polymerase holoenzyme (Kaboord and Benkovic, *Curr. Biol.* 5: 149–57, 1995).

Alternatively, a DNA polymerase that has a 5'→3' exonuclease activity may be used. For instance, such a DNA polymerase may be useful for amplifying short nucleic acid fragments that automatically dissociate from the template nucleic acid after nicking.

According to the method of the present invention, a DNA polymerase may be mixed with target nucleic acid before, after, or at the same time as, a nicking agent is mixed with the target nucleic acid. Preferably, the nicking-extension reaction buffer is optimized to be suitable for both the nicking agent and the DNA polymerase. For instance, if N.BstNB I is the nicking agent and exo⁻ Vent is the DNA polymerase, the nicking-extension buffer can be 0.5×N.BstNB I buffer and 1×DNA polymerase Buffer. Exemplary 1×N.BstNB I buffer may be 10 mM Tris-HCl, 10 mM MgCl$_2$, 150 mM KCl, and 1 mM dithiothreitol (pH 7.5 at 25° C.). Exemplary 1×DNA polymerase buffer may be 10 mM KCl, 20 mM Tris-HCl (pH 8.8 at 25° C.), 10 mM (NH$_4$)$_2$SO$_4$, 2 mM MgSO$_4$, and 0.1% Triton X-100.

Also preferably, the nicking and extension reactions are performed under isothermal conditions. As used herein, "isothermally" and "isothermal conditions" refer to a set of reaction conditions where the temperature of the reaction is kept essentially constant during the course of the amplification. An advantage of the amplification method of the present invention is that there is no need to cycle the temperature between an upper temperature and a lower temperature. Both the nicking and the extension reaction will work at the same temperature or within the same narrow temperature range. However, it is not necessary that the temperature be maintained at precisely one temperature. If the equipment used to maintain an elevated temperature allows the temperature of the reaction mixture to vary by a few degrees this is not detrimental to the amplification reaction. For instance, both the nicking reaction using N.BstNB I (New England Biolabs) and the extension reaction using exo⁻ Bst polymerases (BioRad) may be carried out at about 55° C. Other polymerases that are active between about 50° C. and 70° C. include, but are not limited to, exo⁻ Vent (New England Biolabs), exo⁻ Deep Vent (New England Biolabs), exo⁻ Pfu (Strategene), exo⁻ Bca (Panvera) and Sequencing Grade Taq (Promega). Restriction endonucleases that nick a hemimodified RERS and that are active between about 50° C. and 65° C. include, but are not limited to Bsr I, BstN I, BsmA I, Bsl I and BsoB I (New England BioLabs), and BstO I (Promega).

The extension/amplification reaction may be carried out in the presence of a labeled dideoxyribonucleoside triphosphate so that the label is incorporated into the amplified nucleic acid fragments. Labels suitable for incorporating into a nucleic acid fragment, and methods for the subsequent detection of the fragment are known in the art, and exemplary labels include, but are not limited to, a radiolabel such as $^{32}$P, $^{33}$P, $^{125}$I or $^{35}$S, an enzyme capable of producing a colored reaction product such as alkaline phosphatase, fluorescent labels such as fluorescein isothiocyanate (FITC), biotin, avidin, digoxigenin, antigens, haptens or fluorochromes. The presence of the label in the amplified nucleic acid fragments allows these fragments to function as nucleic acid probes for detecting nucleic acids that are capable of hybridizing with the fragments.

C. Methods for Whole Genome Amplification Involving Multiple Nicking

In another aspect, the present invention provides methods for whole genome amplification that involve multiple nicking in at least one strand of a double-stranded genome ("target genome"). It is a discovery of the present invention that multiple nicking of a target genome, especially a complex genome such as a human genome or a genome of a higher plant, dramatically increases the efficiency of a subsequent amplification of the target genome. "Multiple nicking," as used herein, refers to the nicking at more than one site in at least one strand of a target genome. This step may be used in combination with, or proceeding, any of the known methods of whole genome amplification, especially those that involve the use of PCR or related techniques. Although not wishing to be bound to any particular theory, the inventors of the present invention speculate that multiple nicking of a target genome may relax the topological strains within the target genome and thus facilitate the nucleic acid extension activity of a DNA polymerase.

The target genome of the present invention may be a genome of any organism of interest, including but not limited to, viruses, bacteria, yeast, insects, higher plants and mammals. In a preferred embodiment, the target genome is a human genome. The target genome may be isolated from a whole organism, an organ, a tissue (e.g., a tumor tissue), body fluid (e.g., blood and bone marrow), or a single cell (e.g., a sperm or an oocyte). In certain preferred embodiments, the target genome is isolated from a subject with, or suspected to have, a disease, especially a genetic disease (e.g., Down's Syndrome).

The nicking agent useful in the present invention may be any agent that nicks at multiple sites of at least one strand of a target genome. Detailed description of suitable nicking agents are provided above with respect to descriptions of nucleic acid amplification methods that do not require any external oligonucleotide primers.

A target genome, upon being multiply nicked, may be subsequently amplified using any of the known methods for whole genome amplification. Exemplary whole genome amplification methods include PCR-related amplification methods such as primer-extension preamplification (PEP) (see, e.g., Zhang et al., *Proc. Natl. Acad. Sci. USA* 89: 5847–51, 1992; Zheng et al., *Cancer Epidemiol Biomarkers Prev.* 10: 697–700, 2001), degenerate oligonucleotide-primed PCR (DOP-PCR) (see, e.g., Telenius et al., *Genomics* 13: 718–25, 1992; Speicher et al., *Hum. Mol. Gen.* 2: 1907–14, 1993; Speicher et al., *Am. J. Pathol.* 146; 1332–40, 1995; Kuukasjarvi et al., *Genes Chromosomes Cancer* 18: 94–101, 1997; Vivian et al., *Proc. Natl. Acad. Sci. USA* 93: 14676–9, 1996; Larsen et al., *Cytometry* 44: 317–25, 2001; Barbaux et al., *J. Mol. Med.* 79: 329–32, 2001), ligation-mediated PCR (see, e.g., Christoph et al., *Proc. Natl. Acad. Sci. USA* 96: 4494–9, 1999), tagged PCR (see, e.g., Sun et al., *Nucleic Acids Res.* 23: 3034–40, 1995); and strand displacement amplification (see, e.g., U.S. Pat. Nos. 6,124,120 and 6,280,949).

D. Kits for Nucleic Acid Amplification

The present invention also provides kits for nucleic acid amplification that does not require the use of an external oligonucleotide primer. In some embodiments, the kits include a container containing a nicking agent, another container containing a DNA polymerase and preferably there is an instruction booklet for using the kits. In certain other embodiments, the kits include a container containing both a nicking agent and a DNA polymerase. The nicking agent and DNA polymerase are preferably stored in a state where they exhibit long-term stability, e.g., in suitable storage buffers or in a lyophilized or freeze dried state. In addition, the kits may further comprise a buffer for the nicking agent, a buffer for the DNA polymerase, or both buffers. Alternatively, the kits may further comprise a buffer suitable for both the nicking agent and the DNA polymerase. In some embodiment, the kits may also comprise a container containing a strand displacement facilitator, such as trehalose. Detailed descriptions of various components of the present kits may be found in preceding sections related to various methods of the present invention.

An exemplary nicking agent is a nicking endonuclease N.BstNB I. A suitable buffer for this nicking endonuclease may be 10 mM Tris-HCl, 10 mM $MgCl_2$, 150 mM KCl, 1 mM dithiothreitol (pH 7.5 at 25° C.). N.BstNB I may be stored in the following storage buffer: 50 mM KCl, 10 mM Tris-HCl (pH 7.5), 0.1 mM EDTA, 1 mM DTT, 200 µg/ml BSA, and 50% glycerol.

Exemplary DNA polymerases include exo⁻ Deep Vent, exo⁻ Bst polymerase and exo⁻ Vent. A suitable reaction buffer for these polymerases may be 10 mM KCl, 20 mM Tris-HCl (pH 8.8 at 25° C.), 10 mM $(NH_4)_2SO_4$, 2 mM $MgSO_4$, 0.1% Triton X-100.

The instruction booklet provides information on how to use the kit of the present invention for amplifying nucleic acids without the required use of an external oligonucleotide primer. The information includes descriptions on how to use and/or store the nicking agent and the DNA polymerase, descriptions of buffer(s) for the nicking agent and the DNA polymerase, appropriate reaction temperature(s) and reaction time period(s), etc.

E. Applications of the Nucleic Acid Amplification Methods of the Present Invention As discussed in detail herein above, the present invention provides methods for nucleic acid amplification that do not require the use of an external oligonucleotide primer. These methods will find utility in a wide variety of applications wherein it is necessary, or desirable, to amplify target nucleic acids. Such applications include, but are not limited to, genetic disease diagnosis, tumor dissemination detection, forensics, paleoarcheology, genetic linkage analysis and genetic diversity studies.

For instance, the present method and/or kit may be used in genetic disease diagnosis. Four percent of all newborns are born with genetic defects, indicating the importance of prenatal diagnostics. The present method may be used to amplify genomic DNA isolated from fetal cells obtained from the blood of pregnant women for the assessment of single-gene Mendelian disorders. Another use of the present method is in preimplantation genetic disease diagnosis for in vitro fertilization. DNA from a single sperm, a single oocyte, or individual cells from early embryos or the polar body accompanying the oocyte before fertilization may be amplified according to the present method and/or kit, and the amplified nucleic acid fragments may be used for genetic disease screening before embryo implantation.

Another exemplary application of the methods and kits of the present invention is in the genetic analysis of systematic dissemination of cancer cells from small primary tumors long before clinical metastasis becomes manifest. The amplification of genomic DNA from single disseminated tumor cells allows genomic profiling of these cells and subsequent identification of genotypes that are characteristic for dissemination and ectopic survival. Such identification may facilitate early cancer diagnosis.

As the present method provides a simple and efficient method for amplifying target nucleic acids, it is particularly useful in the circumstances where the amount of the nucleic acids of interest is limited for the intended analysis such as forensic analysis, studies of ancient DNA, genetic linkage analysis and genetic diversity studies.

The following example is illustrative of, and not limiting to, the present invention.

EXAMPLE

Amplification of Human Genomic DNA Using N.BstNBI Nicking Enzyme and Three Different DNA Polymerases Human genomic DNA was obtained from the Coriell Institute (Bethesda Md.) and diluted to 10 ng per microliter with a buffer containing 0.001 M Tris HCl and 0.0005 M EDTA, pH 7.2. Three different reaction mixtures were prepared for three different DNA polymerases (exo- Vent polymerase, exo- Deep Vent polymerase, and Bst polymerase).

Three 50 microliter reaction mixtures were prepared which contained the following:

5 microliters of 10×Thermopol buffer (New England Biolabs (NEB), Milford Mass.);
2.5 microliter of 10×N.BstNBI buffer (NEB);
20 microliters of 1 M trehalose (prepared in ultrapure water);

5 microliters of the genomic DNA at 10 ng/microliter;

1 microliter of N.BstNBI (NEB) (10 units);

0.5 microliters of exo- Vent, exo- Deep Vent, or Bst polymerase at 2000 units/microliter (NEB); and 16 microliter of ultrapure water.

The reaction mixtures were incubated at 60° C. for 60 minutes. After the incubation, the reactions were placed on ice. A small aliquot of each reaction (5 microliters) was diluted 100-fold and the concentration of the nucleic acids was measured at A260. The results are shown in the following table. Nucleic acid amplification was observed in all three reaction mixtures, with Bst polymerase being the most efficient DNA polymerase among the three polymerases tested. The amplified nucleic acid fragments range from about 100 bases to about a few kilobases.

| DNA Polymerase | OD260 Control (no DNA Polymerase) | OD260 with DNA Polymerase | Micrograms Synthesized | Fold Amplified |
|---|---|---|---|---|
| exo-Vent | 0.00028 | 0.0056 | 1.4 | 28 |
| exo-Deep Vent | 0.00029 | 0.034 | 8.5 | 170 |
| Bst | 0.00035 | 0.122 | 30.5 | 610 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for nucleic acid amplification comprising forming a mixture of
   (a) a double-stranded target nucleic acid of which at least one strand has two or more nicking sites;
   (b) a nicking agent capable of nicking at the two or more nicking sites; and
   (c) a DNA polymerase;
   under a condition allowing for the making of two or more copies of at least a portion of the target nucleic acid, wherein the amplification does not require the presence of an external oligonucleotide primer (ODNP) that is capable of specifically annealing to a portion of the target nucleic acid, and is performed by multiple cycles of nicking by the nicking agent and extension by the DNA polymerase.

2. A method for nucleic acid amplification comprising
   (a) multiply nicking at least one strand of a double-stranded target nucleic acid with a nicking agent to provide at least two new 3' termini in that strand;
   (b) extending one or more of the at least two new 3' termini with a DNA polymerase;
   (c) nicking the extension product of step (b) with the nicking agent; and
   (d) extending the nicking product of step (c) to thereby amplify at least a portion of one strand of the target nucleic acid.

3. The method of claim 2 wherein the target nucleic acid is isolated from a single cell.

4. The method of claim 2 wherein the target nucleic acid comprises a whole genome of an organism.

5. The method of claim 4 wherein the organism is a human.

6. The method of claim 2 wherein the nicking agent is a nicking endonuclease.

7. The method of claim 6 wherein the nicking endonuclease is any one selected from the group consisting of N.BstNB I, N.Alv I, N.BbvC I-a and N.BbvC I-b.

8. The method of claim 1 wherein the DNA polymerase is selected from the group consisting of exo⁻ Vent, exo⁻ Deep Vent, exo⁻ Bst, exo⁻ Pfu, exo⁻ Bca, the Klenow fragment of DNA polymerase I, T5 DNA polymerase, Phi29 DNA polymerase, phage M2 DNA polymerase, phage PhiPRD1 DNA polymerase, Sequenase, PRD1 DNA polymerase, 9°Nm™ DNA polymerase, and T4 DNA polymerase homoenzyme.

9. The method of claim 1 wherein the amplification is performed under an isothermal condition.

10. The method of claim 1 wherein the target nucleic acid is isolated from a single cell.

11. The method of claim 1 wherein the target nucleic acid comprises a whole genome of an organism.

12. The method of claim 1 wherein the nicking agent is a nicking endonuclease.

13. The method of claim 2 wherein the DNA polymerase is selected from the group consisting of exo⁻ Vent, exo⁻ Deep Vent, exo⁻ Bst, exo⁻ Pfu, exo⁻ Bca, the Klenow fragment of DNA polymerase I, T5 DNA polymerase, Phi29 DNA polymerase, phage M2 DNA polymerase, phage PhiPRD1 DNA polymerase, Sequenase, PRD1 DNA polymerase, 9°Nm™ DNA polymerase, and T4 DNA polymerase homoenzyme.

14. The method of claim 1 wherein the amplification is performed at 50° C.–70° C.

15. The method of claim 2 wherein steps (a)–(d) are performed at 50° C.–70° C.

16. The method of claim 2 wherein steps (a)–(d) are performed under an isothermal condition.

* * * * *

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Recognition sequence and nicking site of an
      exemplary nicking endonuclease, N.BstNB I
<220> FEATURE:
<221> NAME/KEY: misc_feature
<222> LOCATION: 6,7,8,9,10
<223> OTHER INFORMATION: n = A,T,C or G

<400> SEQUENCE: 1 gagtcnnnnn                                                          10

<210> SEQ ID NO 2
<211> LENGTH: 10
<212> TYPE: DNA
<213> ORGANISM: Artificial Sequence
<220> FEATURE:
<223> OTHER INFORMATION: Recognition sequence and nicking site of an
      exemplary nicking endonuclease, N.BstNB I
<220> FEATURE:
<221> NAME/KEY: misc_feature
<222> LOCATION: 1,2,3,4,5
<223> OTHER INFORMATION: n = A,T,C or G

<400> SEQUENCE: 2 nnnnngactc                                                          10

<210> SEQ ID NO 3
<211> LENGTH: 10
<212> TYPE: DNA
<213> ORGANISM: Artificial Sequence
<220> FEATURE:
<223> OTHER INFORMATION: Exemplary nicking endonuclease sequence that
      nicks outside its recognition sequence  (N.AlwI)
<220> FEATURE:
<221> NAME/KEY: misc_feature
<222> LOCATION: 6,7,8,9,10
<223> OTHER INFORMATION: n = A,T,C or G
```

```
<400> SEQUENCE: 3 ggatcnnnnn                                                           10

<210> SEQ ID NO 4
<211> LENGTH: 10
<212> TYPE: DNA
<213> ORGANISM: Artificial Sequence
<220> FEATURE:
<223> OTHER INFORMATION: Exemplary nicking endonuclease sequence that
      nicks outside its recognition sequence  (N.AlwI)
<220> FEATURE:
<221> NAME/KEY: misc_feature
<222> LOCATION: 1,2,3,4,5
<223> OTHER INFORMATION: n = A,T,C or G

<400> SEQUENCE: 4 nnnnngatcc                                                           10
```